United States Patent

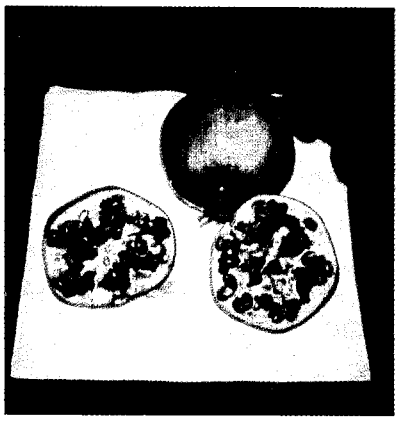

Plant Pat. 3,884

Patented May 11, 1976

3,884

POMEGRANATE TREE

R. J. Owen, 24081 Johns Drive,
Porterville, Calif. 93257

Filed Jan. 21, 1975, Ser. No. 542,848
Int. Cl. A01h *5/03*
U.S. Cl. Plt.—33 1 Claim

This discovery relates to a new and distinct variety of pomegranate tree broadly characterized by regular bearing of early ripening fruit of a bright red color and having a mildly acid pulp enclosing the seeds thereof.

This new variety was discovered as a sport growing in a cultivated area of Wonderful (unpatented) pomegranate trees in my orchard in the San Joaquin Valley in Porterville, Calif. The sport was growing among other pomegranate trees exhibiting the normal characteristic of the Wonderful variety with the exception of its early maturity characteristic. The tree itself resembles the ordinary Wonderful pomegranate. The fruit colors well by September 1 and reaches county specifications at this time. The variety has been asexually reproduced in my orchard in Porterville, Calif. in the San Joaquin Valley by cuttings which were rooted from the recognized sport.

The accompanying illustrations show a specimen of the fruit cut in half and a branch of the subject variety showing foliage and mature fruit.

This variety blooms approximately coincidentally with the Wonderful pomegranate tree. The fruit ripens about two weeks earlier than that of the Wonderful variety and approximately two weeks later than that of the Granada (Plant Pat. 2,618) variety. In further comparison, the seed is less tart than the Wonderful variety and has a mild acid flavor. In relation to the Granada variety, the fruit is larger, is not of as deep purple color, has better shelf life, and matures two weeks later. During the green stage of the fruit the coloring is a light pinkish to red, darkening somewhat the last week in August and first week in September.

Referring more specifically to the pomological details of this new and distinct variety of pomegranate tree, the following has been observed under the climatic conditions prevailing at my grove in the San Joaquin Valley in Porterville, Calif. and is an outline description thereof:

TREE

With respect to size, branches, and leaves, the new variety of pomegranate tree is substantially identical to the Wonderful variety from which it is a sport.

FLOWERS

Blooms approximately coincidentally with the Wonderful variety, if of about the same size and of a brighter red color.

FRUIT

Size: Slight smaller in size (2½" diameter) than that of the Wonderful variety (3" diameter). Form: Typical of pomegranate tree fruit; a semi-globular body having characteristic pomegranate crown.

SKIN

Color when green: Body of fruit is a dark green, while the crown is of a pinkish red. Crown portion of this new variety does maintain a blossom end color throughout its ripening stage and then assumes a bright red coloring throughout the body portion as maturity approaches. Body of the fruit is darkish green approaching crimson in late August. The mature skin color is comparable to that of Wonderful.

COLOR WHEN RIPE

A crimson red color throughout the outside and inside body.

PULP

Less tart than the Wonderful variety, having a mildly acid taste.

MATURITY DATE

Ripens approximately two weeks earlier than the Wonderful. State of California, Department of Agriculture requires that all pomegranates for market contain no more than 1.85% acid. The normal pomegranate season in the San Joaquin Valley begins about the middle of September, at which time the most mature fruit on trees of the Wonderful variety will have less than 1.85% acid. The fruit of the new pomegranate variety ripens the last week in August and first week in September at which time the acid content has been testing between 1.2% to 1.5%. Although the new variety of pomegranate tree possesses the described characteristics under the growing conditions in Tulare County located in the southeastern portion of the San Joaquin Valley, it is to be understood that variation of the usual magnitude in characteristics incident to the growing conditions, fertilization, pruning and pest control is to be expected.

Having thus described and illustrated my new variety of pomegranate tree, I claim:

1. A new and distinct variety of pomegranate tree substantially as illustrated and described and which is characterized by blooming at about the same time as the Wonderful and Granada pomegranate trees, which it very nearly resembles in tree growth and appearance, but from which it is distinguished by the earlier coloring of its fruit, the earlier maturing of the fruit as compared to the Wonderful and the later maturity of its fruit as compared to the Granada.

No references cited.

ROBERT E. BAGWILL, Primary Examiner